(12) United States Patent
Bairamijamal

(10) Patent No.: US 7,375,223 B2
(45) Date of Patent: May 20, 2008

(54) HIGH PRESSURE METHOD FOR PRODUCING PURE MELAMINE IN A VERTICAL SYNTHESIS REACTOR

(75) Inventor: Di Faramarz Bairamijamal, Linz (AT)

(73) Assignee: Ami-Agrolinz Melamine International GmbH, Linz (AT)

( * ) Notice: Subject to any disclaimer, the term of this patent is extended or adjusted under 35 U.S.C. 154(b) by 0 days.

(21) Appl. No.: 11/632,246

(22) PCT Filed: Jul. 27, 2005

(86) PCT No.: PCT/EP2005/008323

§ 371 (c)(1),
(2), (4) Date: Jan. 11, 2007

(87) PCT Pub. No.: WO2006/013079

PCT Pub. Date: Feb. 9, 2006

(65) Prior Publication Data

US 2007/0232801 A1    Oct. 4, 2007

(30) Foreign Application Priority Data

Jul. 29, 2004  (AT)  ............................. A 1298/2004

(51) Int. Cl.
*C07D 251/60*  (2006.01)
(52) U.S. Cl. ...................................... 544/201; 544/203
(58) Field of Classification Search ................ 544/201, 544/203
See application file for complete search history.

(56) References Cited

FOREIGN PATENT DOCUMENTS

| AT | 409 489 B | 8/2002 |
| AT | 410 210 B | 3/2003 |
| WO | 99/00374 A1 | 1/1999 |

*Primary Examiner*—Venkataraman Balasubram
(74) *Attorney, Agent, or Firm*—The Webb Law Firm

(57) ABSTRACT

The invention relates to a high pressure method for producing pure melamine by pyrolyzing urea in a vertical synthesis reactor. The synthesis reactor has three stages above one another: a) in the first stage, the smaller portion of the total amount of urea is introduced into the central tube of a first tank reactor forming a first melamine-containing reaction medium; b) in the second stage, the first melamine-containing reaction medium and the larger portion of the total amount of urea is introduced into the central tube of a second tank reactor forming a second melamine-containing reaction medium; c) in the third stage, the second melamine-containing reaction medium is introduced into a vertical tubular flow reactor forming a raw melamine melt that is processed to obtain pure melamine.

13 Claims, 2 Drawing Sheets

HIGH PRESSURE METHOD FOR PRODUCING PURE MELAMINE IN A VERTICAL SYNTHESIS REACTOR

BACKGROUND OF THE INVENTION

1) Field of the Invention

The present application relates to a high-pressure process for preparing pure melamine by pyrolysis of urea in a vertical synthesis reactor, and to a reactor for carrying out this process.

2) Description of the Related Art

In the high-pressure processes for preparing melamine, generally urea melt and optionally gaseous ammonia are reacted in the absence of a catalyst, for instance at temperatures between 325 and 450° C. and pressures between 50 and 250 bar, to give liquid melamine and offgas consisting mainly of ammonia and carbon dioxide. The liquid melamine which, in addition to unconverted urea, also comprises by-products is subsequently worked up, for example by quenching with water, by sublimation or by decompression under certain conditions, and the pure melamine is subsequently isolated.

The melamine reactors known from the conventional melamine processes are typically vertical tank reactors of the loop reactor type, as described, for example, in AT 409 489 B. Such a reactor has an inner central tube and a heating bundle with circulating salt melt between central tube and reactor wall. The salt melt serves to provide the heat needed for the endothermic melamine synthesis. The urea melt and optionally the ammonia are fed in the lower region of the melamine reactor and react in the outer space between the salt melt-conducting bundle tubes to give melamine melt and offgas. Owing to its low density, the reaction mixture rises upwards, where a separation between melamine melt and offgas takes place. While the offgas is discharged from the reactor and fed to an offgas scrubber, the melamine melt flows downwards in the central tube by virtue of gravity, encounters freshly introduced urea melt there and rises again upwards in the reaction space between the bundle tubes. This circulation of the melamine melt in the synthesis reactor is referred to natural circulation and ensures a certain residence time in the reactor, which is intended to serve for maximum urea conversion to melamine. After the residence time, the melamine melt is discharged via an overflow in the upper reactor region and sent to further workup.

A disadvantage of this melamine reactor is the fact that that ratio of the heat exchange surface area of the bundle tubes to the reaction volume is relatively small, so that relatively high salt melt temperatures are needed for the supply of the heat of reaction needed. These cause increased corrosion on the tube bundle, so that it is necessary to chemically clean the tube bundle annually, which is undesired owing to the production shutdown.

A further disadvantage results from the attainment of a wide residence time distribution in the one-stage loop reactor, i.e. the proportion of unconverted urea in the discharged melamine melt is comparatively high. Since the unconverted urea is discharged together with the by-products in the subsequent melamine workup, this equates to a melamine loss.

EP 0 612 560 describes a vertical melamine reactor consisting of three sections, in which the melamine synthesis takes place in the lowermost sector. The urea melt is conducted downwards via a downpipe from the uppermost region, exits there and reacts in the presence of ammonia between salt melt-conducting tubes to give melamine melt and offgas. The internal melamine circulation in the reactor interior takes place via a central tube. The melamine melt passes through a diaphragm into the sector above, where the offgases are removed from the melt. While the melamine melt is discharged and sent to further workup, the offgas is fed to the uppermost sector, an offgas scrubber, where it is cooled and subsequently discharged.

This reactor too has the disadvantages mentioned of high corrosion and unconverted urea, since it equates to a one-stage loop reactor with regard to reaction control.

WO 99/00374 describes a multistage melamine reactor consisting of a plurality of apparatuses connected in series. The synthesis reactor is a conventional loop reactor. The melamine melt separated from the offgas is subsequently fed to a horizontal tubular reactor in which the urea conversion is to be completed. The reaction mixture is subsequently introduced into an offgas separator and the resulting melamine is sent to further processing. In one variation of the process, a $CO_2$ stripper is connected downstream of the first tubular reactor, then the pressure of the melamine melt is increased, before a further tubular reactor stage and finally an offgas separator follow.

The reactor described has the disadvantage that numerous apparatuses connected in series are needed, which causes high capital costs and a complex design of the plant. In addition, the corrosion problem and the incomplete urea conversion in the loop reactor section exist here too. Since the entire reactor space is taken up by liquid phase in the tubular reactors described and the offgases formed in the melamine formation cannot be removed continuously, it is not possible in these reaction tubes to achieve full urea conversion.

AT 410 210 B discloses a process for preparing melamine by pyrolysis of urea, which urea is introduced into a tank reactor and melamine melt formed in the tank reactor is cooled in a downstream cooling reactor by means of supply of a small amount of urea. The cooling reactor used may be any desired reactor, for example a stirred reactor, a falling-film reactor or else a combination reactor whose upper section is in the form of a tank reactor and whose lower section is in the form of a falling-film reactor. The amount of urea added to the cooling reactor is from about 1 to 5% by weight of the total amount of urea needed to prepare the melamine. In this process, the same disadvantages with regard to the melamine synthesis occur as in a one-stage loop reactor.

SUMMARY OF THE INVENTION

It is accordingly an object of the invention to develop a melamine preparation process using a melamine reactor which does not have the disadvantages mentioned with

DESCRIPTION OF THE PREFERRED EMBODIMENTS

Figure 1:
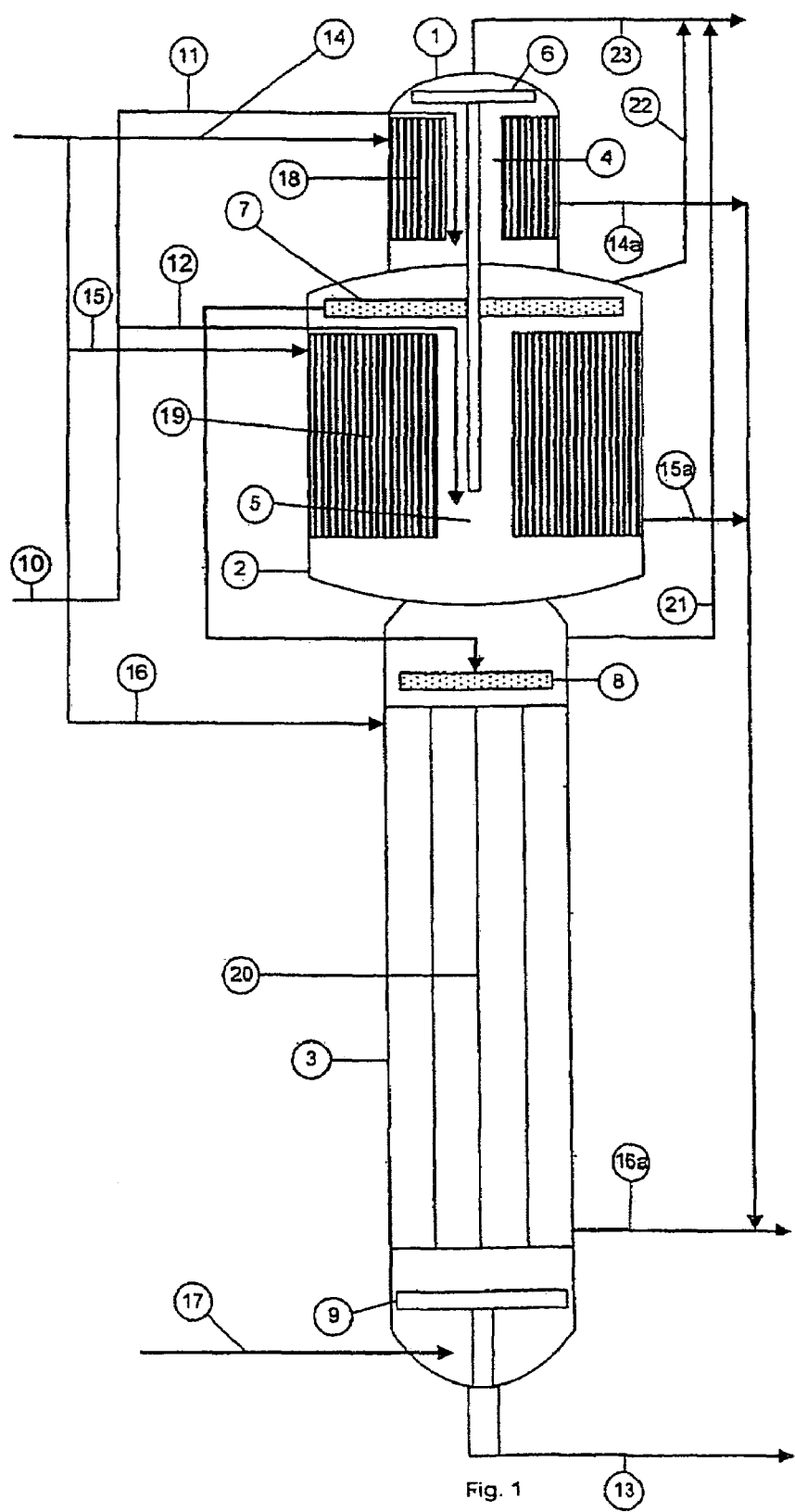
FIG. 1 is a perspective view of an inventive synthesis reactor of the present invention with two loop reactors with natural circulation and a falling-film reactor.

According to the invention, the aim of the object of the invention is achieved firstly by, in a high-pressure process for preparing pure melamine by pyrolysim of urea in a vertical synthesis reactor, the synthesis reactor having three stages arranged vertically one on top of another, and a) in the first, uppermost stage, the smaller portion of the total amount of urea is introduced into the central tube of a first tank reactor and a first melamine-containing reaction medium is formed, b) in the second, middle stage, the first melamine-containing containing reaction medium and the larger portion of the total amount of urea is introduced into the central tube of a second tank reactor and a second melamine-containing reaction medium is formed, and then c) in the third, lowermost stage, the second melamine-containing reaction medium is introduced into a vertical flow tube reactor and a crude melamine melt is formed which is subsequently worked up in any desired manner and pure melamine is obtained.

The inventive division of the total amount of urea between two tank reactors achieves a two-stage stirred tank battery having a narrow residence time distribution, which enables more uniform urea conversion than in the one-stage tank reactor. In addition, gentler and corrosion-reducing supply of the heat of reaction is possible. The combination with the downstream vertical flow tube section ensures optimal reaction control which enables full reaction of the urea. In comparison to other melamine processes, the melamine preparation process according to the invention thus enables more compact, less expensive and more efficient melamine synthesis.

According to the invention, the smaller portion of the total amount of urea is introduced as urea melt into the lower section of the vertical central tube of the uppermost tank reactor. The melt typically has a temperature of about 135 to 300° C. and comes from a urea scrubber in which it has been preheated with the hot reaction offgases. Optionally, gaseous ammonia is also introduced into the first tank reactor. In the tank reactor, between the heating tubes of the tube bundle, the reaction of the urea takes place to give a first melamine-containing reaction medium and offgas at about 330 to 400° C., preferably at about 330 to 380° C., more preferably of about 330 to 360° C. The pressure is about 50 to 600 bar, preferably about 50 to 250 bar, more preferably about 70 to 170 bar. While the offgas is discharged at the top of the tank reactor, the melamine-containing reaction medium flows downwards in the interior of the central tube owing to gravity and rises again upwards after mixing with freshly supplied urea melt. This circulation of the first melamine-containing reaction medium causes a residence time in the first tank reactor which is less than 15 minutes. After the residence time, the first melamine-containing reaction medium is collected at the top of the first tank reactor and flows via a connecting tube into the central tube of the second tank reactor below it.

Together with the first melamine-containing reaction medium, the larger portion of the total amount of urea is introduced as urea melt into the lower region of the vertical central tube of the second tank reactor. Optionally, gaseous ammonia can also be introduced. The temperature, the pressure, the reaction sequence with internal circulation and the residence time in the second tank reactor are the same as in the first tank reactor. The offgas formed is discharged at the top of the second tank reactor. In the second tank reactor, a second melamine-containing reaction medium is formed and is collected at the top of the apparatus and introduced via a connecting tube into the upper section of the flow tube reactor below it. The second melamine-containing reaction medium comprises, on discharge from the apparatus, ammonia, carbon dioxide and by-products. In addition, unconverted urea is present in an amount of about 1 to 3% by weight.

In the vertical flow tube reactor, the second melamine-containing reaction medium flows from the upper into the lower apparatus region owing to gravity. The residence time can be controlled via the vertical height of the flow tube reactor.

During the residence time, the urea which is yet to be converted reacts to give melamine, so that a crude melamine melt is discharged at the lower end of the flow tube reactor and is subsequently sent to any desired further workup. Offgases which are formed are drawn off at the top of the flow tube reactor. The temperature and the pressure in the flow tube reactor is the same as in the first two tank reactor stages.

In a preferred embodiment of the process according to the invention, the smaller portion is 30 to 40% by weight and the larger portion is 70 to 60% by weight of the total amount of urea. In this way, optimal reaction control is achieved in the reactor battery.

Advantageous tank reactors are of the loop reactor type having natural circulation or of the loop reactor type having natural circulation and additional forced convection. In loop reactors, internal circulation is achieved merely by virtue of the different density of the reaction media. Additional stirrer apparatus allows the circulation to be intensified.

Advantageously, the flow tube reactor is a falling-film reactor. The falling-film reactor achieves chemical equilibrium between the reaction partners and thus the possibility of virtually full reaction of the urea at every point over the reactor height. In addition, a falling-film reactor achieves uniform residence time of the melt without axial dispersion around the tubes. Moreover, uniform falling-film thickness prevents material-damaging peak overheating on the reactor tubes.

The tank reactor is preferably a loop reactor having natural circulation, in which the urea is introduced via a tube at whose lower end is disposed an injector in finely divided form into the lower region of each loop reactor.

Preference is further given to the tank reactor being a loop reactor having natural circulation and forced convection with in each case two stirrer units, in which the urea is introduced via a tube close to the stirrer units into the lower region of each loop reactor.

The urea feed in a region of strong flow ensures that good mixing takes place between the urea melt and the circulating melamine-containing reaction medium. The urea feed line tubes can be designed as coaxial tubes, in which case the urea flows in the inner tube and high-temperature insulation made of ceramic is disposed between inner and outer tube.

It is advantageous when gaseous $NH_3$ is introduced from below into the third stage. In this way, the $CO_2$ present in the melamine-containing reaction medium can be removed simultaneously in the flow tube section in countercurrent mode. This saves the capital cost of a separate apparatus for $CO_2$ removal. The removed $CO_2$ is discharged together with the offgas at the top of the apparatus. The temperature of the $NH_3$ introduced may be equal to, higher than or lower than the temperature of the melamine-containing reaction medium in the flow tube section. A further advantage of $NH_3$ introduction is that it decomposes by-products present in the melamine.

Advantageously, the three reactor stages are heated with one salt melt as the heating medium, in which case the salt melt and the melamine-containing reaction medium are conducted in countercurrent in the first and second tank reactor and in cocurrent in the flow tube reactor. This achieves maximum heat introduction in the tank reactor stages with minimum temperature difference between salt melt and melamine-containing reaction medium. In the flow tube stage, this promotes continuous attainment of equilibrium during the reaction.

Particular preference is given to an embodiment of the process in which the temperature in the first, second and third stage is the same and as close as possible to the crystallization point of the melamine at the pressure existing in each case. This can achieve particularly high melamine purity, since the closer the temperature of the melamine is kept to the crystallization point, the lower the content of by-products. A further possibility is to operate the first two stages with the same temperature and the third stage with lower temperature.

It is further preferred for the offgas to be drawn off from each stage and for the offgas streams subsequently to be combined with one another and sent to an offgas scrubber. This enables efficient removal of the offgas at the particular point of formation, so that the attainment of equilibrium in each reaction stage is enabled.

In an advantageous embodiment, the pressure in the first, second and third stage is the same. A pressure equalization line connects all three reactor stages to one another. In this way, the pressure of all three apparatuses can be adjusted by means of a common pressure regulation valve.

The invention further provides a vertical synthesis reactor for carrying out the process according to the invention which has three stages arranged vertically one on top of another, and the first, uppermost stage and the second, middle stage are each tank reactors, in particular loop reactors, comprising central tube and feed lines for urea and optionally $NH_3$, feed lines and draw lines for heating medium, draw lines for offgas and melamine-containing reaction medium, heating units for supplying heat of reaction in the region between central tube and reactor wall, optionally measurement and control units and optionally devices for convection, and the third, lowermost stage is a flow tube reactor comprising feed lines for melamine-containing reaction medium and optionally $NH_3$, feed and draw lines for heating medium, draw lines for offgas and crude melamine melt, heating units for supplying heat of reaction and optionally measurement and control units.

The tank reactors preferably have, in their upper region, collectors which are connected via an internal or external overflow tube for the melamine-containing reaction medium to the central tube of the next lowest stage. This ensures continuous overflow of the melamine-containing reaction medium from the first into the second tank reactor and from there into the flow tube section.

The flow tube reactor preferably has, in its upper region, a distributor for the melamine-containing reaction medium. In this way, uniform division of the melamine over the entire tube cross section is achieved.

Advantageously, the third stage is a falling-film reactor whose cross section is taken up by a tube bundle composed of vertical profiled inner tubes and perforated outer tubes. This achieves a uniform melamine film on the inner tubes and also good heat transfer from the salt melt-conducting outer tubes.

Preference is given to a reactor in which the tank reactors each have two stirrer units and urea feed lines ending in the central tube close to the stirrer units. Useful stirrer units are, for example, impeller stirrers, pitched-blade stirrers or turbine stirrers. Advantageously, the tank reactors have, in the central tube, urea feed lines leading from top to bottom and having an injector at the lower end. This can achieve good mixing between urea and reaction medium.

Preference is given to a reactor which has, as heating units in the tank reactors, bimetallic compound tubes with smooth inner tubes and perforated outer tubes. The inner tubes are flowed through by the melamine-containing reaction medium and the outer tubes by the heating medium. The perforated external tubes achieve optimal heat exchange performance.

Advantageously, the offgas draw lines of the three reaction stages have heatable demisters or droplet separators. In this way, melamine fractions present in the offgas are separated out actually upstream of the offgas scrubber.

The melamine melt discharged from the flow tube section of the synthesis reactor is discharged and subsequently worked up in any desired manner. For example, it can be solidified by decompression and/or cooling or it is transferred into the gas phase and subsequently desublimed. Another means of workup is quenching with an aqueous solution and subsequently crystallizing out the melamine.

Figure 2:
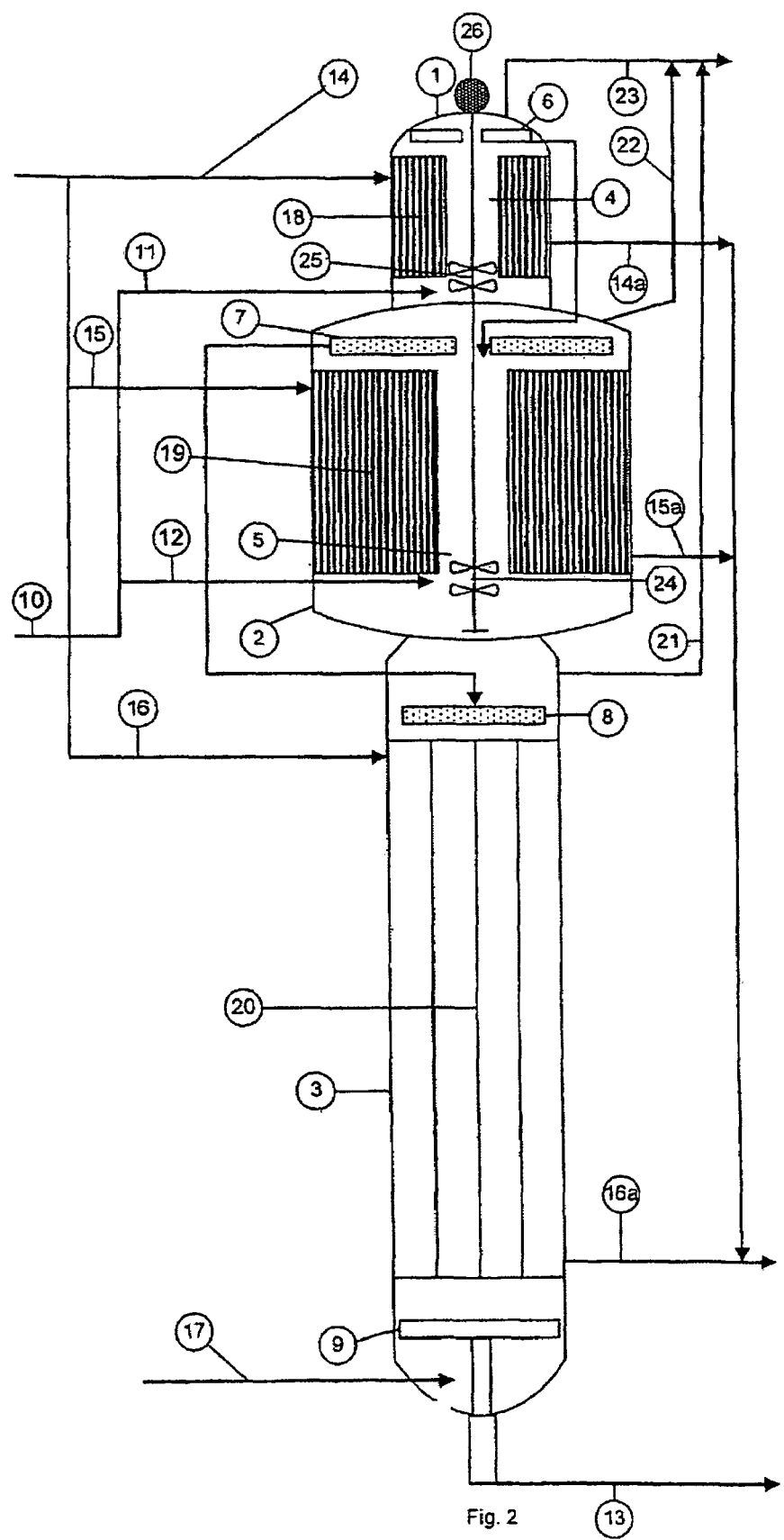
FIG. 2 is a perspective view of an inventive synthesis reactor of the present invention with two loop reactors with natural circulation and additional forced convection and a falling-film reactor.

An exemplary embodiment of the inventive synthesis reactor with two loop reactors with natural circulation and a falling-film reactor is shown in FIG. 1. FIG. 2 shows a further embodiment of the inventive reactor with two loop reactors with natural circulation and additional forced convection and a falling-film reactor.

FIG. 1 and FIG. 2 show: (1) and (2) a first and a second loop reactor with natural circulation, (3) a falling-film reactor, (4) and (5) the central tubes of the first and second loop reactor, (6) a collector and the overflow tube from the first into the second loop reactor, (7) a collector and the overflow tube from the second loop reactor into the falling-film reactor, (8) a distributor, (9) an ammonia distributor, (10) a feed line for all of the urea, (11) and (12) feed lines for the urea stream into the first and second loop reactor, (13) the draw line for the melamine melt for further workup, (14), (15) and (16) feed lines for the salt melt, (14a), (15a), (16a) draw lines for the salt melt, (17) a feed line for $NH_3$ gas, (18), (19), (20) salt melt-conducting bundle tubes as heat exchangers, offgas lines (21) from the falling-film reactor, (22) from the middle reactor and (23) from the uppermost reactor, and (24) and (25) stirrer apparatus with a stirrer motor (26).

The process according to the invention is carried out as follows:

4620 kg/h of urea melt, i.e. about 35% of all of the synthesis urea, are sprayed at a temperature of 230° C. and a pressure of 160 bar via the feed line 11 at whose lower end is disposed an injector (not shown) into the lower region of the central tube 4 of a first loop reactor 1 with natural circulation. The reactor 1 is heated to 347° C. using the bundle tubes 18 by means of salt melt heating. The reaction mixture formed at this temperature and a pressure of 150 bar is separated in the upper region of the loop reactor 1 into offgas consisting of $NH_3$ and $CO_2$, and a first melamine-containing reaction medium. While the offgas is drawn off at the top of the first loop reactor 1 via the offgas line 23 and sent to an offgas scrubber (not shown), the melamine-containing reaction medium passes via the collector and the overflow tube 6 into the central tube 5 of the second loop reactor 2 with natural circulation below it. The second loop reactor 2 is heated to 347° C. using the bundle tubes 19, likewise by means of salt melt; the pressure is the same as in the first loop reactor 1. Simultaneously with the first melamine-containing reaction medium, 8580 kg/h of urea melt at a temperature of 230° C. and a pressure of 160 bar are fed to the second loop reactor via the feed line 12. This corresponds to about 65% by weight of all of the synthesis urea. In the second loop reactor 2, a second melamine-containing reaction medium and offgas are formed at 347° C. and 150 bar. The offgas is drawn off at the top of the loop reactor via the offgas line 22 and led off to the offgas scrubber (not shown).

The second melamine-containing reaction medium is conducted via a collector and the external overflow tube 7 from the second loop reactor 2 to the top of a falling-film reactor 3 kept at 370° C. using the bundle tubes 20 by means of salt melt. The salt melt flows via the feed line 16 through the jacket tubes of the tube bundle 20 taking up the reactor cross section into the draw line 16a. The distributor 8 divides the melamine into substreams which flow through the inner tubes of the tube bundle 20 from top to bottom. In countercurrent to the descending melamine, gaseous ammonia at 345° C. in an amount of 1350 kg/h is introduced via the distributor 9 from below via the feed line 17 in order to remove $CO_2$ present in the melamine. The pressure in the falling-film reactor is the same as in the two loop reactors. At the top of the falling-film reactor, the gas formed is discharged via the offgas line 21 together with the $CO_2$ removed and sent to the offgas scrubber (not shown). At the bottom of the falling-film reactor, a melamine melt having a by-product content of <1% by weight is discharged via the draw line 13. The melamine melt is subsequently introduced at 347° C. and 150 bar into a quencher (not shown) and quenched there with an aqueous solution, and the pure melamine is subsequently crystallized out of the resulting melamine solution.

The invention claimed is:

1. A high-pressure process for preparing pure melamine by pyrolysis of urea in a vertical synthesis reactor, wherein the synthesis reactor has three stages arranged vertically one on top of another, and
   a) in the first, uppermost stage, a smaller portion of a total amount of urea is introduced into a central tube of a first tank reactor and a first melamine-containing reaction medium is formed,
   b) in the second, middle stage, the first melamine-containing reaction medium and a larger portion of the total amount of urea is introduced into a central tube of a second tank reactor and a second melamine-containing reaction medium is formed, and then
   c) in the third, lowermost stage, the second melamine-containing reaction medium is introduced into a vertical flow tube reactor and a crude melamine melt is formed which is subsequently worked up in any desired manner and pure melamine is obtained.

2. The process according to claim 1, wherein the smaller portion of the total amount of urea is 30 to 40% by weight and the larger portion of the total amount of urea is 70 to 60% by weight.

3. The process according to claim 1, wherein the tank reactor is a loop reactor having natural circulation or a loop reactor having natural circulation and forced convection.

4. The process according to claim 1, wherein the flow tube reactor is a falling-film reactor.

5. The process according to claim 1, wherein the tank reactor is a loop reactor having natural circulation and the urea is introduced via a tube at whose lower end is disposed an injector in finely divided form into the lower region of each loop reactor.

6. The process according to claim 1, wherein the tank reactor is a loop reactor having natural circulation and forced convection with in each case two stirring units, and the urea is introduced via a tube close to the stirring units into the lower region of each loop reactor.

7. The process according to claim 1, wherein gaseous $NH_3$ is introduced from below into the third stage.

8. The process according to claim 1, wherein the three stages are heated with a salt melt, and the salt melt and the melamine-containing reaction medium are conducted in countercurrent in the first and second tank reactor, and in cocurrent in the flow tube reactor.

9. The process according to claim 1, wherein the temperature in the first, second and third stage is the same and as close as possible to the crystallization point of melamine at the pressure existing in each case.

10. The process according to claim 1, wherein the offgas is drawn off from each stage and the offgas streams are subsequently combined with one another and sent to an offgas scrubber.

11. The process according to claim 1, wherein the pressure in the first, second and third stage is the same.

12. The process according to claim 2, wherein the tank reactor is a loop reactor having natural circulation or a loop reactor having natural circulation and forced convection.

13. The process according to claim 2, wherein the flow tube reactor is a falling-film reactor.

* * * * *

UNITED STATES PATENT AND TRADEMARK OFFICE
CERTIFICATE OF CORRECTION

PATENT NO. : 7,375,223 B2  Page 1 of 1
APPLICATION NO. : 11/632246
DATED : May 20, 2008
INVENTOR(S) : Bairamijamal It is certified that error appears in the above-identified patent and that said Letters Patent is hereby corrected as shown below:

Title Page;
Face of the Patent, see Item (56) References Cited, FOREIGN PATENT DOCUMENTS, add the following foreign reference:

-- EP   612 560 A1          8/1994 --

Signed and Sealed this

Second Day of December, 2008

JON W. DUDAS
*Director of the United States Patent and Trademark Office*